US011816750B2

(12) United States Patent
Clancy et al.

(10) Patent No.: US 11,816,750 B2
(45) Date of Patent: Nov. 14, 2023

(54) SYSTEM AND METHOD FOR ENHANCED CURATION OF HEALTH APPLICATIONS

(71) Applicant: Quintiles IMS Incorporated, Danbury, CT (US)

(72) Inventors: Brian Clancy, Newport, RI (US); Michael Ian Krupnick, Danbury, CT (US)

(73) Assignee: IQVIA Inc., Parsippany, NJ (US)

( * ) Notice: Subject to any disclaimer, the term of this patent is extended or adjusted under 35 U.S.C. 154(b) by 396 days.

(21) Appl. No.: 15/633,268

(22) Filed: Jun. 26, 2017

(65) Prior Publication Data
US 2018/0374174 A1     Dec. 27, 2018

(51) Int. Cl.
| | |
|---|---|
| *G06Q 50/22* | (2018.01) |
| *G06Q 10/10* | (2023.01) |
| *G16H 10/60* | (2018.01) |
| *G16H 40/63* | (2018.01) |
| *G16H 50/20* | (2018.01) |
| *G16H 50/30* | (2018.01) |

(52) U.S. Cl.
CPC ............. *G06Q 50/22* (2013.01); *G06Q 10/10* (2013.01); *G16H 10/60* (2018.01); *G16H 40/63* (2018.01); *G16H 50/20* (2018.01); *G16H 50/30* (2018.01)

(58) Field of Classification Search
CPC ........ G06Q 50/22; G06Q 10/10; G06Q 50/24; G16H 10/60; G06F 19/328
USPC .......................................................... 705/2
See application file for complete search history.

(56) References Cited

U.S. PATENT DOCUMENTS

| | | | |
|---|---|---|---|
| 10,467,304 B1* | 11/2019 | Lin | H04L 67/10 |
| 2013/0124523 A1* | 5/2013 | Rogers | G16H 10/60 |
| | | | 707/737 |
| 2014/0236846 A1* | 8/2014 | Melika | G06Q 10/06 |
| | | | 705/310 |
| 2014/0244296 A1 | 8/2014 | Linn et al. | |
| 2015/0012283 A1 | 1/2015 | Ryan et al. | |
| 2015/0100328 A1 | 4/2015 | Kress et al. | |
| 2016/0063212 A1* | 3/2016 | Monier | G16H 50/50 |
| | | | 705/3 |
| 2016/0117469 A1* | 4/2016 | Tesanovic | G16H 40/20 |
| | | | 705/3 |
| 2017/0011182 A1* | 1/2017 | Whitehurst | G06Q 10/10 |

\* cited by examiner

*Primary Examiner* — Jonathon A. Szumny
*Assistant Examiner* — Christopher B Wehrly
(74) *Attorney, Agent, or Firm* — Fish & Richardson P.C.

(57) ABSTRACT

A computer-implemented method includes a first module of a computing system receiving application-specific data for determining utilization attributes of multiple application programs. A second module of the system receives data for determining patient archetypes. A third module of the system determines a clinical benefit of each application program based on analysis of the application-specific data. The system matches an application program with a particular patient archetype based on analysis of each patient archetype and the determined clinical benefit of the application program. The system selects a particular application program for use by a patient of a first patient group based on: i) a characteristic of the first patient group that is included in a first patient archetype; and ii) the clinical benefit of the particular application exceeding a threshold clinical benefit.

24 Claims, 6 Drawing Sheets

SYSTEM AND METHOD FOR ENHANCED CURATION OF HEALTH APPLICATIONS

BACKGROUND

This specification relates to enhanced curation of health applications.

An electronic device may download one or more applications from an online application store and an example user may cause the device to invoke or execute the downloaded application. Examples of applications include executable program files for games, photo editing software, and social networking applications. Applications or executable program files designed specifically for mobile deployment on mobile operating systems may be referred to as "apps."

An application or app can be a program file that an electronic computing device executes on behalf of a user and the application may include a series of instructions to accomplish a given task based on input from the user. In some instances, tasks that a user wants to accomplish may be related to health care and medical treatment. Some applications may be developed specifically for use by various parties in managing information related to health care tasks, such as helping a patient to monitor a condition, allowing a doctor to gather and analyze information to treat patients more effectively, or allowing health care companies, such as pharmaceutical companies, to aggregate data and draw conclusions that support their business.

SUMMARY

According to the disclosed technologies, a data ingest module of a computing system receives application-specific data for determining utilization attributes of multiple application programs and a patient archetype module of the computing system receives data for determining patient archetypes. Each patient archetype may include at least one characteristic that is descriptive of one or more patient groups. A clinical prediction module of the computing system determines a clinical benefit of each application program based on analysis of the application-specific data.

The computing system may execute a matching algorithm to match an application program with a particular patient archetype based on analysis of each patient archetype and the determined clinical benefit of the application program. The computing system selects a particular application program for use by a patient of a first patient group based at least on: i) a characteristic of the first patient group that is included in a first patient archetype; and ii) the clinical benefit of the particular application exceeding a threshold clinical benefit.

One aspect of the subject matter described in this specification can be embodied in a computer-implemented method performed using a computing system that includes one or more modules. The method includes, determining, by a first module of the one or more modules and using multiple datasets that include application-specific data, utilization attributes of respective applications of multiple applications; determining, by a second module of the one or more modules and using the multiple datasets, multiple patient archetypes, each patient archetype including at least one characteristic that is descriptive of one or more patient groups.

For each application of the multiple applications, the method includes: determining, by a third module of the one or more modules, a clinical benefit of the application based at least on analysis of the application-specific data, the clinical benefit capable of being provided to one or more patients when the one or more patients use the application; and executing, by the computing system, a matching algorithm to match the application with a particular patient archetype based on analysis of each patient archetype and the determined clinical benefit of the application.

The method further includes, selecting, by the computing system, a particular application for use by a patient of a first patient group, the particular application being selected based at least on: i) a characteristic of the first patient group that is included in a first patient archetype; and ii) the clinical benefit of the particular application exceeding a threshold clinical benefit.

These and other implementations can each optionally include one or more of the following features. For example, in some implementations, the method further includes: receiving, by the computing system, data that indicates a medical characteristic of the patient; determining, by the computing system, that the indicated medical characteristic corresponds to at least the characteristic of the first patient group included in the first patient archetype; and in response to determining, providing, by the computing system and for output to a user device, the selected particular application.

In some implementations, the medical characteristic is associated with a particular medical condition of the patient and the clinical benefit of the particular application is provided based on application content that is advantageous for improving the particular medical condition of the patient.

In some implementations, executing the matching algorithm to match the application with the particular patient archetype, comprises: identifying one or more characteristics included in the particular patient archetype; determining that the clinical benefit of the application exceeds the threshold clinical benefit; in response to determining that the clinical benefit of the application exceeds the threshold clinical benefit, matching the application with the particular patient archetype based on the clinical benefit being associated with at least one characteristic included in the particular patient archetype.

In some implementations, the multiple datasets include one or more types of application-specific data, the one or more types comprising at least one of: i) application ratings that include respective application ratings generated by patients or medical professionals about the application; ii) technical attributes of the application that correspond to one or more application functions enabled by program code of the application; iii) application use data that indicates one or more usage attributes about the application; and iv) demographic data that indicates one or more patient attributes about patients that use the application.

In some implementations, the first module is a data ingest module configured to: analyze data elements of the application-specific data included in respective datasets of the multiple datasets; in response to analyzing the data elements, link the one or more types of application-specific data by associating a first type of application-specific data with at least a second type of application-specific data; and determine the utilization attribute based on the linked one or more types of application-specific data.

In some implementations, the second module is a patient archetyping module configured to determine multiple distinct patient archetypes, each patient archetype being determined based on at least one of: i) user-specified input used by the computing system to define an archetype to include user-defined characteristics that are descriptive of the one or more patient groups; or ii) machine learning logic used by the computing system to define an archetype based on analysis of the multiple datasets, the archetype being defined to include characteristics that are descriptive of the one or more patient groups.

In some implementations, the third module is a benefits prediction analytics module configured to at least one of: i) receive at least a first type of application-specific data, and use at least one predictive algorithm to analyze the first type of application-specific data to determine at least one health outcome to be improved by the clinical benefit of the application; or ii) receive at least a second type of application-specific data received by the first module, and use at least one predictive algorithm to analyze the second type of application-specific data to determine at least one health outcome to be improved by the clinical benefit of the application.

In some implementations, the application is one of multiple applications associated with an application database and the benefits prediction analytics module is configured to: access the application database to generate a ranked listing of applications, wherein the applications in the listing of applications are ranked based on a determined clinical benefit of each application.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. The described subject matter enables efficient analysis of patient data and health application utilization data to determine a clinical benefit that can be provided to a patient by one or more health applications. A computing system uses data analysis modules to efficiently identify and select health applications that can aid in the medical treatment process of a patient.

The described teachings can enable full and comprehensive adoption of health apps in a prescriptive and integrated manner and can enable improved health outcomes and cost-savings through the proliferation of mobile health apps. Health apps can be integrated with existing healthcare systems and systematically prescribed by providers, as opposed to self-determined by consumers. Technology solutions of this specification can enable healthcare providers to confidently assess and navigate the available health apps.

System and methods according to the described teachings enables use of deep-learning and predictive analytics to generate patient archetypes and for efficient matching of identified health applications with one or more patient groups. Such analytical processes enable computations for patient archetypes determination and health application matching with archetypes to be performed rapidly and efficiently.

The deep-learning algorithms cause the system to learn optimal, or more efficient, matching sequences that enhance computational efficiency of processors of the computing system. Such enhanced efficiency may result in reduced processor utilization and memory access operations relative to data processing operations. Thus, system throughput may be increased thereby leading to more efficient processor and memory utilization.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

As part of the health care process, physicians or other medical care providers may suggest, request, or "prescribe" patients use a health, wellness, or disease management application as part of the patient's medical treatment. For example, such an application may be a mobile or web application.

The use of health-related applications designed for mobile devices is emerging as a means of increasing patient engagement in their health and reducing health system costs. Physicians can have interest in prescribing a particular health application for their patients and payers (e.g., insurance companies) may have an interest in promoting, to their members, the use of health applications designed for mobile or other electronic devices. Other groups including employers, patient organizations and pharmaceutical companies may also have an interest in promoting the use of health applications.

There are a number of application programs in the health or medical categories for that are available for download through online app stores. This can make finding the most effective or appropriate health application difficult for certain patients. In some instances, certain patients may have a particular medical condition and may require, not only effective health applications, but also applications that are uniquely configured to provide treatment options for their particular condition.

According to the disclosed technologies, systems and methods are provided for enhanced identification, curation, and selection of health applications that can provide a clinical benefit to particular patients. A first module of a computing system receives application-specific data for determining utilization attributes of multiple application programs and a second module of the computing system receives data for determining patient archetypes. Each patient archetype may include at least one characteristic that is descriptive of one or more patient groups. A third module of the computing system determines a clinical benefit of each application program based on analysis of the application-specific data.

The computing system may execute a matching algorithm to match an application program with a particular patient archetype based on analysis of each patient archetype and the determined clinical benefit of the application program. The computing system selects a particular application program for use by a patient of a first patient group based at least on: i) a characteristic of the first patient group that is included in a first patient archetype; and ii) the clinical benefit of the particular application exceeding a threshold clinical benefit.

Figure 1:
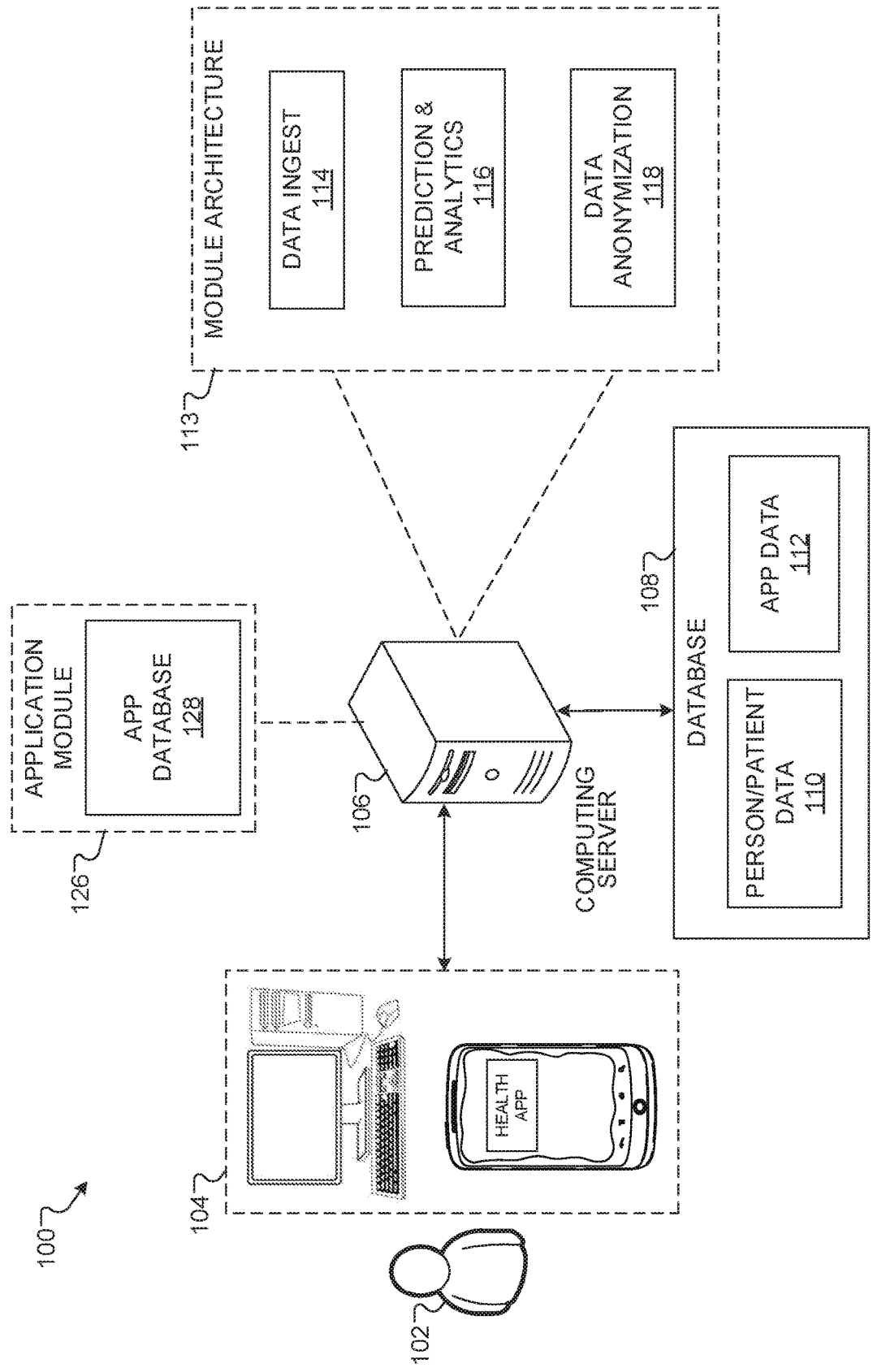
FIG. 1 shows a block diagram of an example computing system for enhanced curation of health applications.

FIG. 1 shows a block diagram of an example computing system 100 for enhanced curation of health applications. System 100 can include multiple computers, computing servers, and other computing devices that each include processors and memory that stores compute logic or software instructions that are executable by the processors. In some implementations, multiple computers can form a cluster computing node, while multiple nodes can form node clusters. Cluster computing nodes and/or node clusters may be used to perform example computational and/or machine learning processes described herein for accomplishing enhanced curation of health applications.

System 100 includes a user device(s) 104, a computing server 106, and a database 108. Although depicted in FIG. 1 at least as a desktop computer console or smartphone, user device 104 can be any known computer system, such as a desktop computer, a laptop computer, a tablet device, a mobile device, a smartphone or any other related computing device that receives user input.

In general, user device 104 is configured to receive user input from a human user 102 and system 100 can analyze or process the user input to cause server 106 to perform computational operations that are responsive to the user input. As discussed in more detail below, in some implementations, the user input may be a user command or query in which user 102 seeks a response from system 100.

For example, user 102 can be physician that seeks to identify one or more health applications having an indicated health benefit that can be used by a patient of the physician (or by the physician) to treat or improve an existing medical condition of the patient. Alternatively, user 102 can be a patient, or any other individual, that seeks to identify one or more health applications having an indicated health benefit that can be used to treat or improve an existing medical condition of a particular person or healthcare patient.

User device 104 may be one of multiple computing devices that are disposed within an example computer network and the network can generally include at least one database or storage device that stores database 108. As described in more detail below, database 108 can include one or more datasets that include patient data 110 and application-specific data ("app data") 112. App data may be used herein interchangeably with application-specific data, or application data.

Server 106 can include one or more processors, memory, and data storage devices that collectively form one or more computing systems of server 106. The processors of the computing systems process instructions for execution by server 106, including instructions stored in the memory or on the storage device to display graphical information for a graphical user interface (GUI) on an example display of, for example, user device 104. Execution of the stored instructions can cause one or more of the actions described herein to be performed by server 106.

In other implementations, multiple processors may be used, as appropriate, along with multiple memories and types of memory. For example, server 106 may be connected with multiple other computing devices, with each device (e.g., a server bank, groups of servers, modules, or a multi-processor system) performing portions of the actions or operations associated with the various processes or logical flows described in this specification.

Database 108 can be stored within an example data storage device such as a computing resource(s) configured to store large amounts of data (e.g., large datasets exceeding 5 terabytes (TB) or more). Example computing resources for data storage can include various electronic data storage devices that use electrical power to store and retrieve data. The data can be stored in either an analog format or a digital format and can be stored on a variety of media. Example data storage devices can include hard drives, server based storage devices, or cloud storage systems including multiple distinct devices.

System 100 can receive information or data associated with or about multiple patients. For each patient with regard to whom data has been received, patient data 110 may include any information related to the patient's overall health, such as one or more medical conditions of the patient, or prescription therapies or pharmaceutical products being used by the patient.

Patient data 110 can include or correspond to a patient's electronic medical record (EMR), including EMR data inclusive of lab results. A patient's EMR can provide a digital or electronic representation of the patient's hardcopy or paper medical chart and can include some or all information about the patient's medical history. Server 106 is configured to access database 108 to receive or obtain patient data 110 and app data 112 to perform one or more operations that involve matching, or associating, at least one application with at least one patient identified in patient data 110 (described below).

As shown in FIG. 1, server 106 can include, or be configured to access, software instructions or computing logic associated with computational functions associated with computing modules of module architecture 113. As described in more detail below, module architecture 113 can include computing functions for data ingest 114, predication and analytics 116, and data anonymization 118. Server 106 can be further configured to include, or access, an application module ("app module") 126 that provides data communications with an example application database 128.

Application database 128 can include a variety of application programs. Such applications can provide a patient with the ability to track medical data, provide treatment recommendations, and may be generally configured to aid in the medical care process of a patient. Thus, the variety of applications included in database 128 can be therapeutic interventions that have a meaningful role in the health care process of a patient.

As indicated above, an application or application program can be a general term that refers to instructions on a computing platform to accomplish a given task. As used herein, "wireless device application" and "app" can refer to applications that run on a mobile operating system. Such apps or wireless device applications can be obtained from an online app store and database 128 can correspond to, or be configured to access, an example online app store for obtaining data about the variety of health applications that may be accessible via database 128.

Implementations described in this specification provide methods for obtaining data about the variety of applications that may be included in application database 128. The data can include app utilization data that, upon analysis by server 106, can provide practical insights regarding overall effectiveness of such applications. An example measure of an application's effectiveness may relate to the applications ability to provide a clinical benefit to a user, aid in the medical treatment of a patient, or aid in making economic decisions related to medical care progress of a user.

An application program or health application can include any software program or on-patient device capable of providing various streams of data that can be received and analyzed by system 100. For example, a health application can correspond to a wearable fitness or health related device that tracks and indicates a person/patient's steps for a particular time period (e.g., 10,000 steps in one day) or a person's heart rate during an exercise session (e.g., 130 beats per minute during a run).

In some implementations, a person's wearable device, e.g., a fitness tracker, a smart watch, or a geo-watch, can include software applications and other program code related to geo-tagging or geo-location features for indicating the person's location. Similarly, a person's vehicle can include program code for tracking the vehicle's cabin/internal air quality (and temperature) as well as software related to geo-location features. These software programs may provide data streams that include parameters indicating person's or device/vehicle's geo-location.

Hence, such data streams can be used by system 100 to determine when a particular person/patient visits certain locations (e.g., fast food locations associated with high fat/salt/sugar items, health food store, vitamin shop, etc.). As described in more detail below, these data streams can be analyzed by system 100 and used by the system to determine health characteristics of a person or patient based at least on the particular locations. Moreover, system 100 can use the analyzed data streams to recommend one or more health applications for a person or patient.

Referring again to module architecture 113, data ingest 114 can correspond to data ingest computing functions of server 106. Example data ingest functions can include server 106 receiving and analyzing a variety of data (e.g., app-specific data) relevant to determining utilization attributes about respective health applications of the multiple various applications that are accessible via app database 128. Other example data ingest functions can include server 106 receiving and analyzing patient level data (PLD) that is accessible via database 108.

Predication and analytics 116 can correspond to determination, data analysis, data grouping, and predictive computing functions of server 106. Example predictive and data analysis functions can include server 106 analyzing the variety of app-specific data for determining utilization attributes about the respective health applications accessible via app database 128. Other example predication and analytics functions can include server 106 analyzing the PLD accessible via database 108. Based on the analysis of the app-specific data and PLD, server 106 can then predict or determine which health applications have the highest predictive clinical benefit for particular patient medical conditions.

Data anonymization 118 can correspond to data analysis, data modification, and anonymization computing functions of server 106. Example data anonymization functions can include server 106 analyzing and modifying received PLD to remove personally identifiable information for a person or patient included in database 108. Other example data anonymization functions can include server 106 generating one or more data partitions to segment identifiable patient/person data that must be accessed for certain computing tasks and to segment de-identified patient/person data that must be accessed for certain other computing tasks.

While this specification refers to wireless device applications and apps as being used in certain implementations, the descriptions in this specification can be relevant to other types of applications. In some example implementations of this specification, described health application functions can be directed to applications that are wireless device applications, or apps, while in other implementations health application functions can also correspond to scenarios in which the applications are meant to run on a desktop or laptop PC, or are provided by web browsers.

Figure 2:
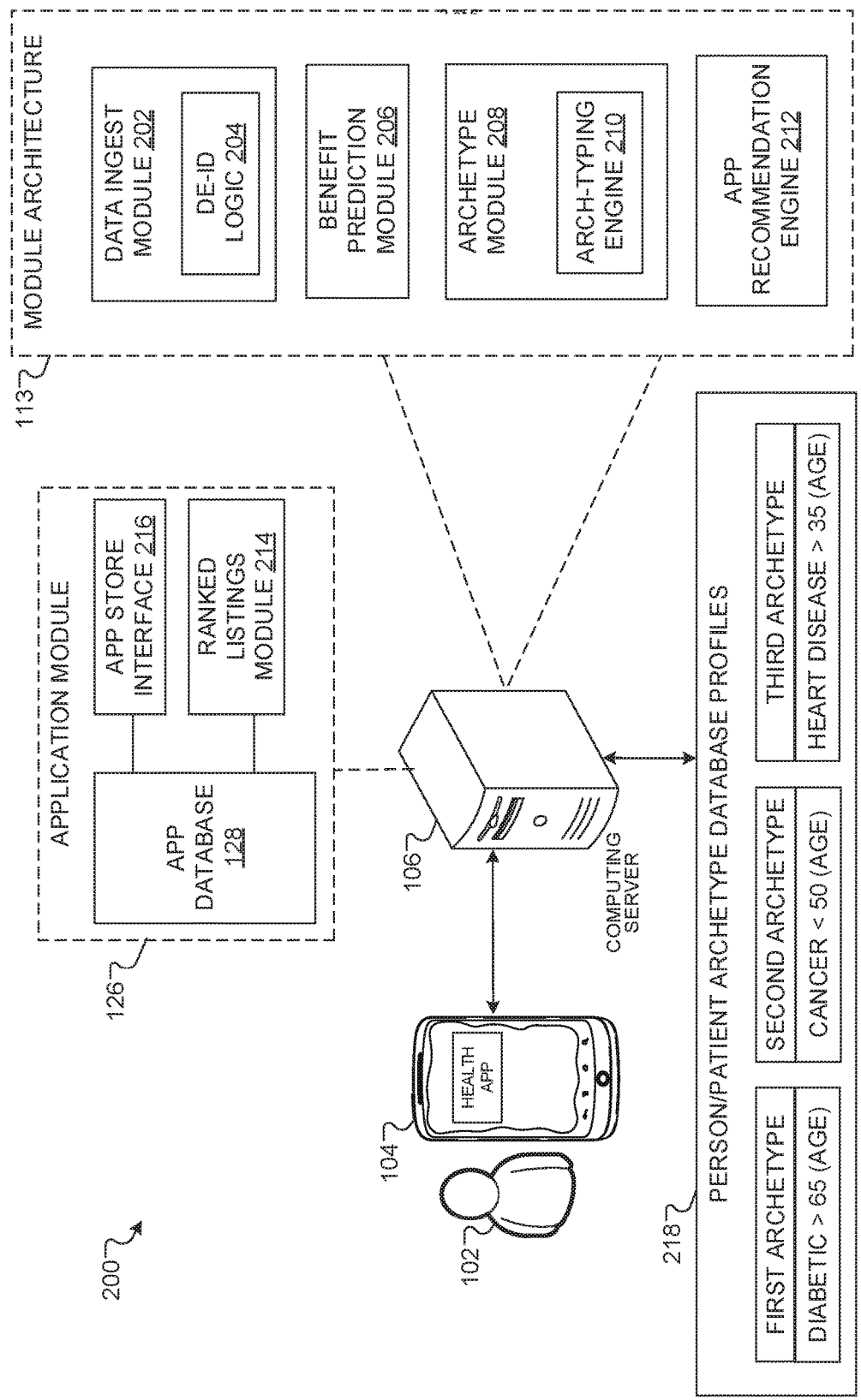
FIG. 2 shows a block diagram of modules associated with the example computing system of FIG. 1.

FIG. 2 shows a block diagram of modules associated with a computing system 200. System 200 can be a sub-system of the system 100 described above with reference to FIG. 1. As shown, system 200 generally includes a data ingest module 202, a benefit prediction module 206, an archetype module 208, and a recommendation engine 212.

As used in this specification, the term "module" is intended to include, but is not limited to, one or more computers configured to execute one or more software programs that include program code that causes a processing unit(s) of the computing device to execute one or more functions. The term "computer" is intended to include any data processing or computing devices/systems, such as a desktop computer, a laptop computer, a mainframe computer, a personal digital assistant, a server, a handheld device, or any other device able to process data.

Data ingest module 202 includes de-identification logic 204 and can be used to implement the example computing functions discussed above for data ingest 114 and data anonymization 118. As noted above, server 106 can access database 108 to receive patient data 110 and app data 112 to perform one or more operations that involve matching, or associating, at least one application program with at least one patient identified in patient data 110.

For example, server 106 can use computing logic of data ingest module 202 to access app database 128 to obtain app data 112 for storage in database 108. In some implementations, app module 126 can include an app store interface 216 that facilitates access to app database 128. In some implementations, interface 216 can be an example application program interface (API) for accessing a variety of app specific data for the various health applications of app database 128.

In general, computing logic of server 106 can include software instructions for one or more APIs (e.g., interface 216) that are associated with data ingest functions of module 202. For example, the software instructions can include sets of coded routines and/or proprietary protocols for receiving, processing, and exchanging data communications between app database 128 and one or more other computing devices of systems 200 (or system 100).

Server 106 can receive, via app module 126 and module 202, a variety of app data 112 for storage in database 108 and for analysis by one or more modules of architecture 113. For example, server 106 can receive app data 112 related to: i) patient reviews of an app; ii) professional reviews of an app; iii) app functionality; iv) app endorsement; v) app developer attributes; vi) clinical literature about an app; vii) assessments about app developers; viii) open source information about an app; ix) cohort-level anonymized patient level app engagement data such as app utilization patterns (e.g., times opened in a day); and x) app-collected biometric data (e.g., blood glucose data). App data related to patient reviews of an app can be associated with, or extracted from, app store user ratings and app reviews that may exist for respective health applications of app database 128.

App data 112 related to patient reviews of an app can also include app utilization data and patient review comments for a particular health application and that have been aggregated by app database 128. Example utilization data can include the number of downloads of a particular health application or a retention parameter for a particular health application (e.g., 30-day retention). In some implementations, module 202 can be configured to parse data from free text app reviews that have been submitted by users and that are accessible via app database 128 or via other data sources. App data 112 related to professional reviews of an app can include ratings or review content about health applications for patients by individual healthcare professionals.

App data 112 related to app functionality can include one or more features or elements of an application's function. For example, app data 112 related to an app's functions can include an app's ability to provide reminders (e.g., pill consumption reminders), to receive and process patient blood pressure data, to receive and process patient blood sugar data, or to perform a variety of other health related functions. In some implementations, module 202 can be configured to parse data from free text app descriptions that describe various health application functions and that are accessible via app database 128 or via other data sources.

App data 112 related to app endorsement can include endorsement data of health applications by certain health application publishers, healthcare institutions, government agencies, or various other institutions or entities associated with evaluation of health care related apps. App data 112 related to app developer attributes can include characteristics of the app's developer and their attention to the app's improvement or development. For example, developer attributes or characteristic can include the industry of the developer, the number of other apps owned by the developer, the reviews and ratings of the other apps, as well as the developer's update cadence for their respective apps.

App data 112 related to clinical literature about an app can include published literature expressing clinical assessments regarding app usability, app clinical outcome benefits, app safety features, or various other data indicating an app's performance in a clinical environment. In some implementations, module 202 can be configured to parse data from various digital or electronic clinical literature/resources (e.g., online/PDF formatted literature resources) that provide clinical assessments and descriptions about various health applications. In some instances, the digital/electronic literature resources may be accessible via app database 128 or via other digital data sources.

App data 112 related to assessments about app developers can include developer assessment surveys (e.g., self-assessment surveys). For example, assessment surveys can include app developers', or app users', responses/answers to survey questions regarding various aspects of a healthcare apps usability or functions. In some implementations, assessment surveys can be crafted to obtain insights or data about privacy/security features of a health application or to gain insight about clinical benefits that may be provided to a patient that uses a particular health app.

App data 112 related to "open source" information about an app can include various sources of data that are free and open for public access or use. In some implementations, the open source data can be acquired either through utilization of an application scripting platform or via business transactions with individual app developers and/or various online/virtual application program stores.

Server 106 can also receive, via app module 126 and module 202, app data 112 relating to app utilization metrics and/or app behavioral data/biomarkers for storage in database 108 and for analysis by one or more modules of architecture 113. For example, app utilization and behavioral data can include data relating to types of users or patients that used an app, a particular app was used, or an explicit or implicit purpose for the patient having used the app. An explicit purpose can include recorded goals, while an explicit purpose can include inferred rationales. An inferred rationale can include system 200 determining or inferring that a patient reasoning for using a weight loss app is because the patient wants to lose weight, particularly if patient data 110 indicates that the patient is over-weight.

App utilization and behavioral data can also include data relating to when an app is used by a patient, such as each date and time of day at which an app is used. In some implementations, data relating to when an app is used can be inclusive of when an app ingests/receives or exchanges data communications with other apps. Some utilization and behavioral data can include location data associated with where an app is used. Location data can include Global Positioning System (GPS) coordinates and other inferred information including received signal indications that an app is used at a user's "home," a user's "work," or a user's "car."

Other utilization and behavioral data can include form factors that are associated with use of an application as well as the duration of use of an app and a spend parameter that indicates user spending per use of an app. Example form factors can include the app being used as a smartphone app, as a web-based app, as a tablet-based app (e.g., iPad, Samsung tablet), as a desktop computer app, a smart-watch app, a streaming device app (e.g., Apple TV, Roku, etc.). Other form factors can include use of visual commands or voice commands that invoke app functions, active use of an app, e.g., active user input via an app interface, and passive use of an app, e.g., app executes as a background computing process and with infrequent user input.

As indicated above, server 106 can receive patient data 110 (e.g., PLD) including data associated with multiple patients. In addition to the above descriptions, patient data 110 can also include information about patient demographics including patient age, patient gender, and patient payer type, as well as app exposure and app utilization data. For example, such data can indicate which patients received or downloaded certain health applications as well as any utilization or behavioral data patterns associated with a patient's use of particular applications.

As also indicated above, server 106 can receive, via app module 126 and module 202, a variety of app data 112 that corresponds to multiple data streams received from applications or on-person wearable devices. For example, the streams of data can indicate a person/patient's daily step count, sleep patterns, daily heart rate, or instances in which a person's step count or heart rate exceeds a threshold heart rate for indicating an exercise frequency of the person. Further, the streams of data can include geo-location information that indicates when a particular person/patient visits certain locations generally associated with healthy or unhealthy practices (e.g., person visiting the gym, bar, fast food restaurant, health food store, etc.).

In some instances, data streams received by system 200 can indicate that a patient has a propensity to visit locations that sell food items or other consumer content (e.g., drugs, abused substances, unsavory content, etc.) that can diminish or degrade health characteristics of the person. For example, the diminished health characteristics of the person may occur when items or content are consumed in large quantities. In other instances, analyzed data streams provided by wearable devices can indicate that a person/patient with heart disease does not exceed a certain number of steps or does not exceed a certain heart rate at least one or two times per week.

De-identification (de-ID) logic 204 can be used to de-identify detailed app utilization and behavioral patterns. In some instances, de-ID logic 204 can be configured to de-identify inherently complex personally identifiable data, such as location data that indicates a health application is being, or has been, used at specific address location. In general, de-ID 204 is used to ensure that PLD data accessible by an example app or user device 104 does not include personally identifiable information such that data privacy and security requirements can complied be with.

For example, server 106 can use de-ID logic 204 to scan patient data 110, identify one or more data fields associated with personally identifiable information (PII), and extract, remove, or modify the PII to preclude PII access by an example health application executed via user device 104. In some implementations, server 106 can be configured to filter patient data 110 that is accessible by health applications to ensure the applications do not receive or gain unauthorized access to patient PII.

Patient data 110 can also include patient claims data and patient EMR data inclusive of lab results. In some implementations, different types of received patient data 110 can be associated with distinct data "siloes" of database 108 and system 100, 200 can be configured to link or integrate two or more distinct types of data. For example, system 200 can link or integrate a first data silo of PLD/patient data 110 related to app exposure and utilization data with a second data silo of PLD related to contents of a patient's EMR.

As described in more detail below, received patient and app data can be stored in database 108 and server 106 can access database 108 to obtain patient data 110 and app data 112 to perform operations for matching, or associating, patients identified in patient data 110 with certain health applications.

Data anonymization 118 can correspond to data analysis, data modification, and anonymization computing functions of server 106. Example data anonymization functions can include server 106 analyzing and modifying received PLD to remove personally identifiable information for a person or patient included in database 108. Other example data anonymization functions can include server 106 generating one or more data partitions to segment identifiable patient/person data that must be accessed for certain computing tasks and to segment de-identified patient/person data that must be accessed for certain other computing tasks.

Benefit prediction module 206 is generally configured to determine one or more health application benefit prediction outcomes based one analytical processes enabled by computing logic of module 206. For example, module 206 can be configured to analyze patient data 110 and app data 122 to identify, determine, or predict which health apps of app database 128 have the highest predictive clinical benefit.

Module 206 can utilize processes and equations associated with predictive analytics. For example, predictive analytics inputs to an example equation can include non-app health metrics, such as the distinct types of patient data 110 described above and app-specific metrics, such as the various types of app data 112 described above, including app identity and app utilization pattern data. Predictive analytics output can include, correspond to, a variety of health outcomes that can be associated with use of a particular health application (e.g. reduced hospitalizations, increased survival rate, etc.).

In some implementations, module 206 can use the predictive analytics output data to generate a listing of health applications that include health outcomes or predicted patient clinical benefits that exceed a threshold benefit. For example, module 206 can analyze the analytics inputs and can generate a numerical indicator (0.8) that quantifies a predicated clinical benefit of a health application. Module 206 can then compare the numerical indicator for the predicted clinical benefit to a threshold clinical benefit indicator (0.6).

Module 206 can then generate a listing of health applications that have a predicted clinical benefit that exceeds the threshold, as indicated by the numerical indicator for each health application. In some implementations, module 206 can access an example ranked listings module 214, of application module 126, to generate a ranked listing of health applications that have predicted clinical benefits that exceed a threshold benefit. For example, the generated listing can include multiple health applications that are ranked by their respective overall likelihood for generating particular clinical health outcomes that are beneficial to a patient based on the patient's use of the application.

Archetype module 208 can be configured to determine one or more seeded or user-defined person/patient archetypes. For example, with reference to user-defined archetypes, a system administrator of system 100 can manually define certain person/patient archetype profiles 218, such as an archetype profile for persons/patients that are diabetic and over the age of 65 (i.e., diabetics>65). After at least one person/patient archetype profile is defined by an example user or system administrator, system 100 can then analyze or leverage health application benefit prediction outcomes generated by module 206 to identify health applications.

For example, system 100 uses prediction outcomes generated by module 206 to determine health applications that have the highest predicted clinical benefit for a particular person/patient group. In general, the clinical benefit is capable of being provided to one or more patients of a particular archetype when the one or more patients use the health application.

In some implementations, module 208 can be configured to generate one or more system defined archetypes. For example, system 100, 200 can utilize one or more deep learning or other related predictive analytics models to determine or identify a sufficient number of person/patient archetypes. Hence, module 208 can receive/access person/patient data 110 and app data 112 and use deep learning or predictive analytics to analyze the data to detect recurrent data patterns and to determine multiple archetypes based on the analysis. Each determined patient archetype can include at least one characteristic that is descriptive of one or more patient groups, e.g., cancer patient archetype profile for cancer patients under the age of 50.

In some instances, system 100 uses module 208 to determine multiple patient archetype profiles so as to optimize health outcomes and clinical benefits for large patient groups that have with a particular medical condition. For example, system 100 can use deep learning or predictive analytics to determine that, instead of defining patient archetype profiles by patient age and medical condition, it may actually be more optimal to define patient groups primarily by their app utilization patterns (e.g., utilization patterns to-date) and only secondarily by their current health condition.

Module 208 can include an archetype engine 210 configured to receive and ingest certain identified person/patient EMR data (e.g., patient age, patient gender, patient lab data, etc.) via an example API or health system message interface. Archetype engine 210 can be an example person/patient archetype definition sub-module of module 208 that initially matches individual persons or patient groups to an archetype as defined by the archetype engine.

In some implementations, archetype engine 210 performs ongoing person/patient archetype matching analysis by periodically analyzing person/patient health or medical characteristics. This periodic analysis enables archetype engine 210 to detect changes in a patient's medical status. In some instances, health or medical status changes of a person can trigger a change in a person's archetype which may also indicate an opportunity to change or update one or more health applications that were previously recommended for a person.

Archetype engine 210 can receive the variety of app data 112 that corresponds to multiple data streams received from vehicle based computing systems or applications, or on-person wearable devices. As noted above, the data streams can indicate one or more health characteristics of a person, such as the person's exercise frequency or whether the person has a propensity to visit locations that are associated with healthy or unhealthy life practices.

In some implementations, archetype engine 210 can use the data streams to determine whether a particular subset of persons or patients are appropriate candidates for one or more clinical trials. In some instances, a subset of patients may be enrolled in a current clinical trial program and archetype engine 210 uses the various data streams to identify and analyze at least one behavioral factor of respective patients of the subset. In some implementations, identified behavioral factors can be confounders which have the potential to positively or negatively affect an overall outcome of a clinical trial program.

For example, one or more behavioral factors can be indicative of a particular patient's quality of life, and where the particular patient may be also enrolled in a clinical trial program. Patient behavioral factors and quality of life indicators that are not controlled for during a clinical trial may be affect evaluations of certain health-related interventions associated with the trial. In this context, the data streams received from vehicle based applications or on-person wearable devices can provide digital behavioral biomarkers for analysis by system 200. Hence, system 200 can use the analyzed data streams to identify confounders that should be controlled for during a clinical trial. Similarly, digital biomarker data can be analyzed and used by system 200 to generate archetype profiles that indicate persons/patients that may be preferred or ideal candidates for certain clinical trial programs.

Recommendation engine 212 can be configured to recommend one or more health applications based on a particular archetype of a patient as determined by archetype engine 210. In some implementations, engine 212 can execute one or more matching algorithms to match a health application with a particular patient archetype based on analysis of each patient archetype and the determined clinical benefit of the health application.

An example learning algorithm may be optimized on patient outcomes for personalized patient matching with selected health applications. A learning algorithm can be configured to match patient groups with appropriate apps and to improve the matching and app selection to optimize and improve clinical benefit outcomes.

Engine 212 can be configured to generate user interfaces associated with certain visual applications that can respond to touch input and other user input gestures. Likewise, engine 212 can be configured to generate user interfaces associated with certain verbal applications configured to respond to voice commands or to ambient patient-health care provider dialogue. These applications can be used via example smartphone based health applications, web-based health applications, or via API-enabled health applications, e.g., application scripting platforms that integrate to a patient's EMR.

Engine 212 can provide fully automated health application delivery and app recommendation functions. For example, engine 212 can be configure to automatically respond to incoming patient data 110 based on "standing orders" from a treating physician. For example, a scripting application may provide a treating physician with certain "borderline cases" and can receive data from the physician regarding certain actions the physician may take during particular patient treatment scenarios.

The scripting application can enable a physician to configure an example physician profile that includes various treatment preferences for a given medical and treatment scenario. Engine 212 can be configured to reference a physician's profile, analyze the physician's treatment preferences, and provide or push recommended apps and related medical devices to one or more patients based not only on the patient's archetype but also on the physician's treatment preferences and on the timing of the patient's visit to the physician.

Figure 3A:
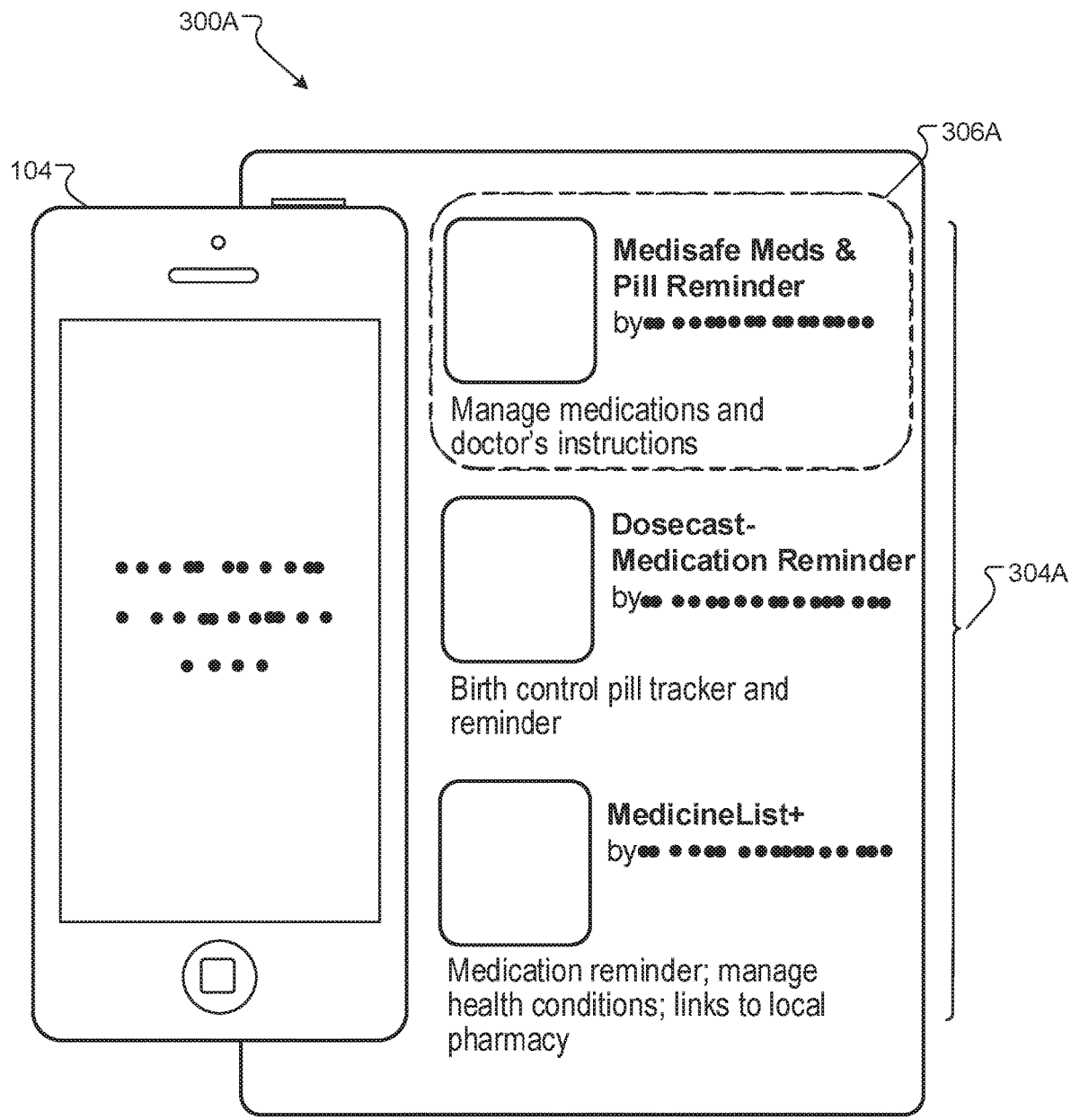
FIGS. 3A and 3B shows an example user device and respective representations of example health applications identified based on the described methods for enhanced curation of health applications.
Figure 3B:
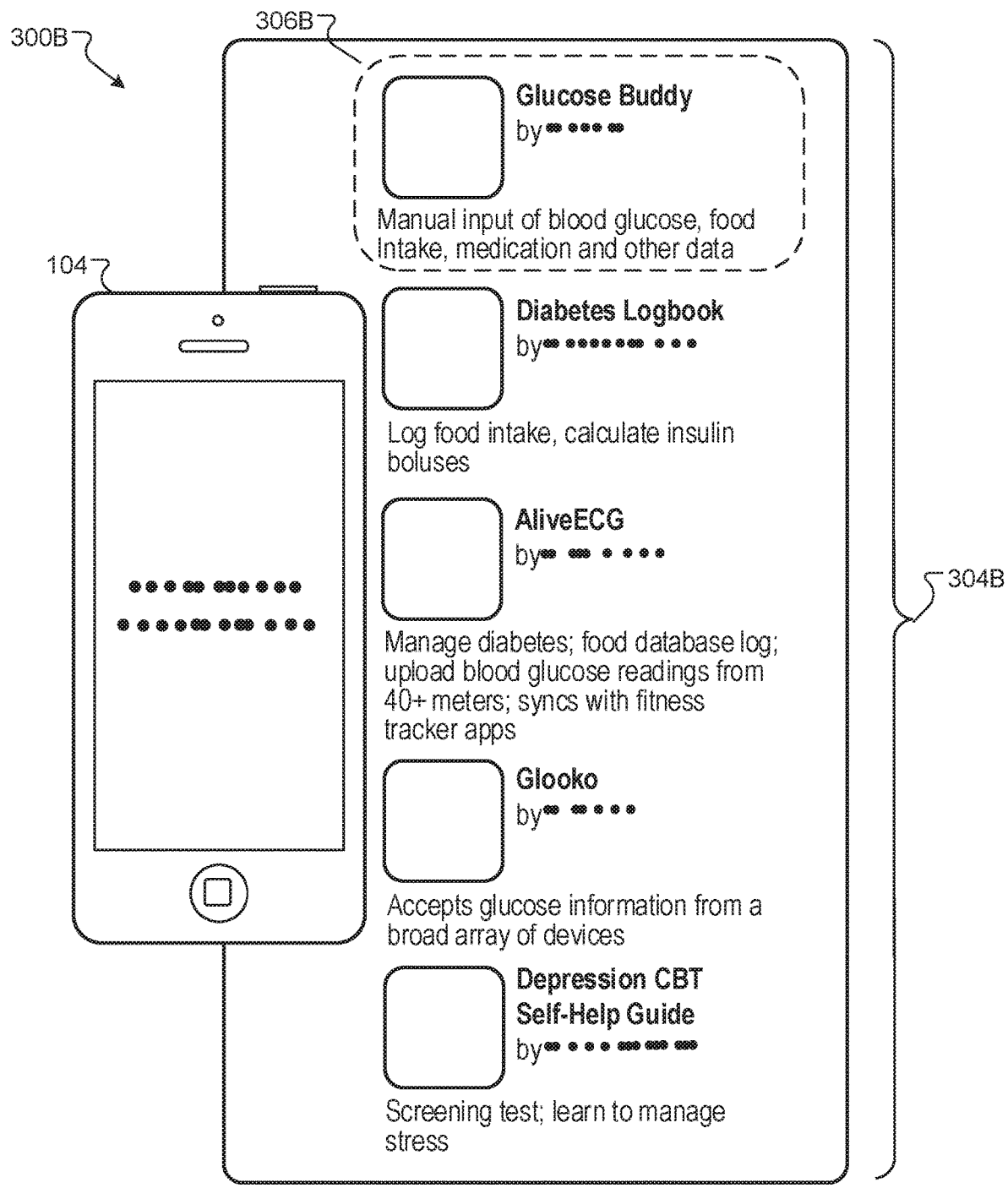

FIGS. 3A and 3B show an example user device and respective representations 300A and 300B of example health applications that can be identified based on the described methods for enhanced curation of health applications. As shown, user device 104 can include application grouping 304A that includes example health application 306A, while application grouping 304B includes example health application 306B.

As shown, health application 306A can be a medisafe health application used by patients to manage consumption of medicines and pills based on reminder notifications generated by application 306A. In general, application 306A can include a clinical benefit that exceeds a threshold benefit and may have been matched to a particular patient of database 108 based on the patient having a medical condition that requires frequent consumption and management of various medicines and physician instructions.

As shown, health application 306B can be a Glucose buddy/monitoring health application used by patients to manage/monitor consumption or intake of food, medicines and other items that may have the potential to adversely impact a patient's blood glucose levels. In general, application 306B can include a clinical benefit that exceeds a threshold benefit and may have been matched to a particular patient of database 108 based on the patient's diabetic condition. The patient's diabetic condition can be indicated by an example archetype profile 218 for which the patient has been assigned.

Figure 4:
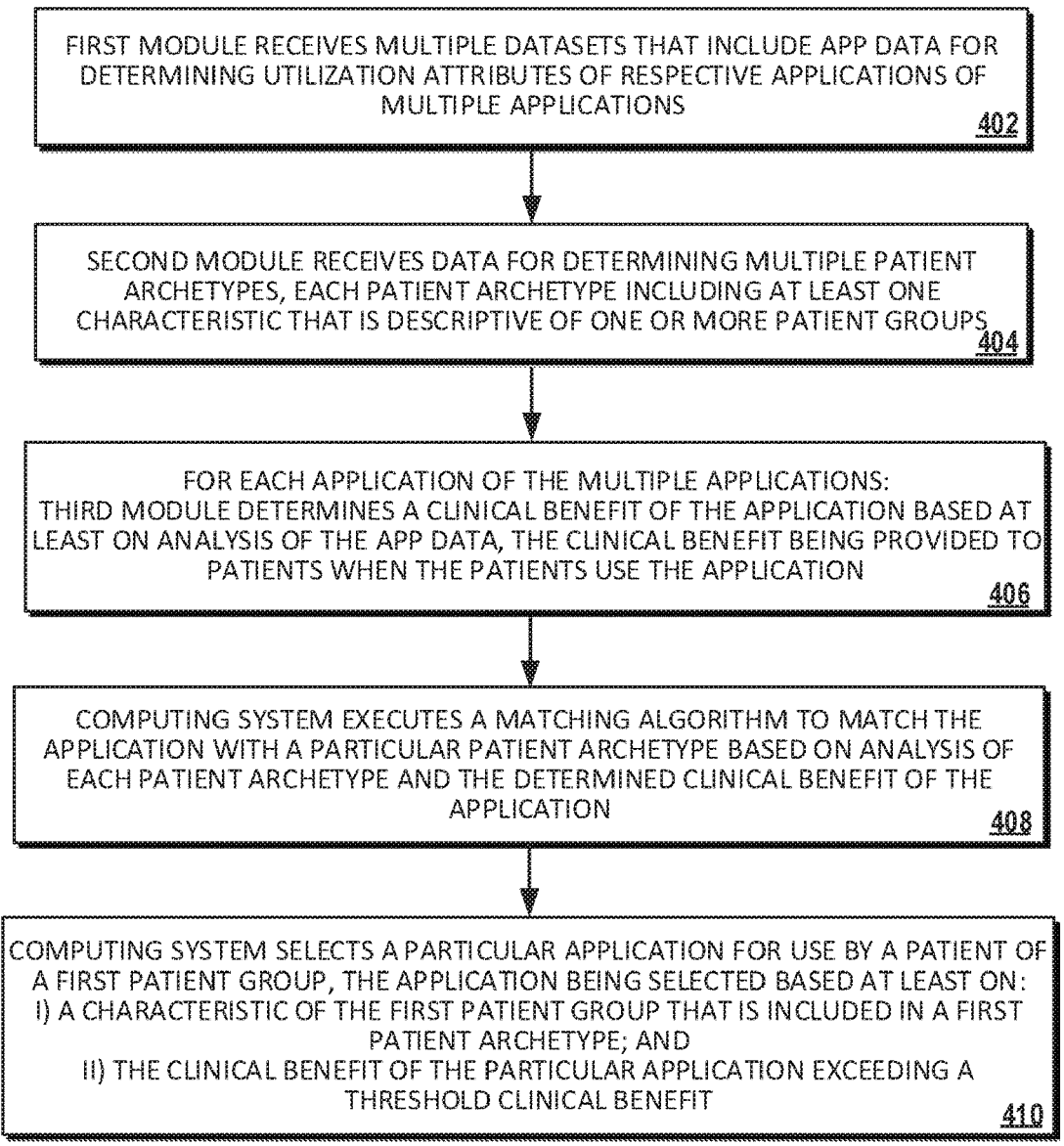
FIG. 4 shows a flow diagram of an example process for enhanced curation of health applications.

FIG. 4 shows a process flow diagram of an example process 400 for enhanced curation of health applications. Process 400 can be implemented using system 100 and system 200 described above. Thus, descriptions of process 400 may reference one or more of the above-mentioned computing resources of systems 100 and 200. In some implementations, the described actions of process 400 can be enabled by computing logic or programmed instructions executable by a processor and memory of an example electronic device, such as server 106 or user device 104 described above.

At block 402 of process 400, system 100 receives, using data ingest module 202, multiple datasets that include application-specific data 112. Data 112 is used to determine utilization attributes of respective applications of multiple applications associated with user device 104. At block 404, patient archetype module 208 receives a plurality of data for determining multiple patient archetypes. Each patient archetype includes at least one characteristic (e.g., diabetic over the age of 65) that is descriptive of one or more patient groups.

In some implementations, each patient archetype is determined based on at least one of: i) user-specified input which system 100 uses to define an archetype; or ii) machine learning logic (e.g., deep learning/predictive analytics) used by system 100 to define an archetype based on analysis of the multiple datasets. In some instances, the archetype is defined to include characteristics that are descriptive of the one or more patient groups.

In some implementations, execution of process 400 includes use of deep-learning and predictive analytics to generate patient archetypes. In some instances, deep-learning and predictive analytics are implemented using the above described systems to enable efficient matching of identified health applications with one or more patient groups based on the generated patient archetypes. Such deep-learning and analytical processes enable computations for patient archetype determination and health application matching with archetypes to be performed rapidly and more efficiently relative to current systems.

At block 406, for each application of the multiple applications, benefit prediction module 206 determines a clinical benefit of the application based at least on analysis of the application-specific data 112. In general, the clinical benefit is capable of being provided to one or more patients when the one or more patients use the application. At block 408, process 400 includes system 100 executing a matching algorithm to match the application with a particular patient archetype based on analysis of each patient archetype and the determined clinical benefit of the application.

At block 410, system 100 selects a particular application for use by a patient of a first patient group. In some implementations, the particular application is selected based at least on: i) a characteristic of the first patient group that is included in a first patient archetype; and ii) the clinical benefit of the particular application exceeding a threshold clinical benefit.

In some implementations, executing the matching algorithm to match the application with the particular patient archetype includes system 100 identifying one or more characteristics included in the particular patient archetype and determining that the clinical benefit of the application exceeds the threshold clinical benefit.

In response to determining that the clinical benefit of the application exceeds the threshold clinical benefit, system 100 can match the application with the particular patient archetype based on the clinical benefit being associated with at least one characteristic included in the particular patient archetype. For example, the at least one characteristic included in the particular patient archetype can be a particular type of diabetes (e.g., type-2). Further, the clinical benefit associated with the at least one characteristic can be related to improvements in a patient's resistance to insulin and/or improvements in an amount of insult produced by the patient's body.

In other implementations, system 100 is configured to execute deep-learning algorithms to cause one or more modules (e.g., module 208) of the system to learn optimal, or more efficient, matching sequences. Use of deep-learning algorithms for optimal or more efficient matching processes can enhance computational efficiency of one or more processors of system 100. Such enhanced efficiency may result in reduced processor utilization and memory access operations relative to data processing operations of the matching sequences. Thus, throughput of system 100 can be increased thereby leading to more efficient processor and memory utilization.

In some implementations, process 400 can include system 100 receiving data that indicates a medical characteristic of the patient and the system determining that the indicated medical characteristic corresponds to at least the characteristic of the first patient group included in the first patient archetype. In response to this determination, system 100 can provide the selected particular application for output to user device 104 (e.g., as shown via FIG. 2).

For example, the first patient group can be a group of patients where respective patients of the group each have differing types of diabetic conditions and are each over the age of 65. Hence, the first patient archetype can be generally described as diabetics over 65. The medical characteristic can be associated with a particular medical condition of the patient. As indicated in the preceding example, the particular medical condition can be diabetes, whereas the medical characteristic associated with the particular medical condition can be a type of diabetes, e.g., type-1 diabetes, or type-2 diabetes.

In general, the clinical benefit of the particular application is provided based on application content that is advantageous for improving the particular medical condition of the patient. For example, the associated medical characteristic and particular medical condition can collectively correspond to type-2 diabetes. For this medical condition and characteristic, the particular application and corresponding content can be used by a patient to cause improvements in their body's overall resistance to insulin or overall production of insulin.

Figure 5:
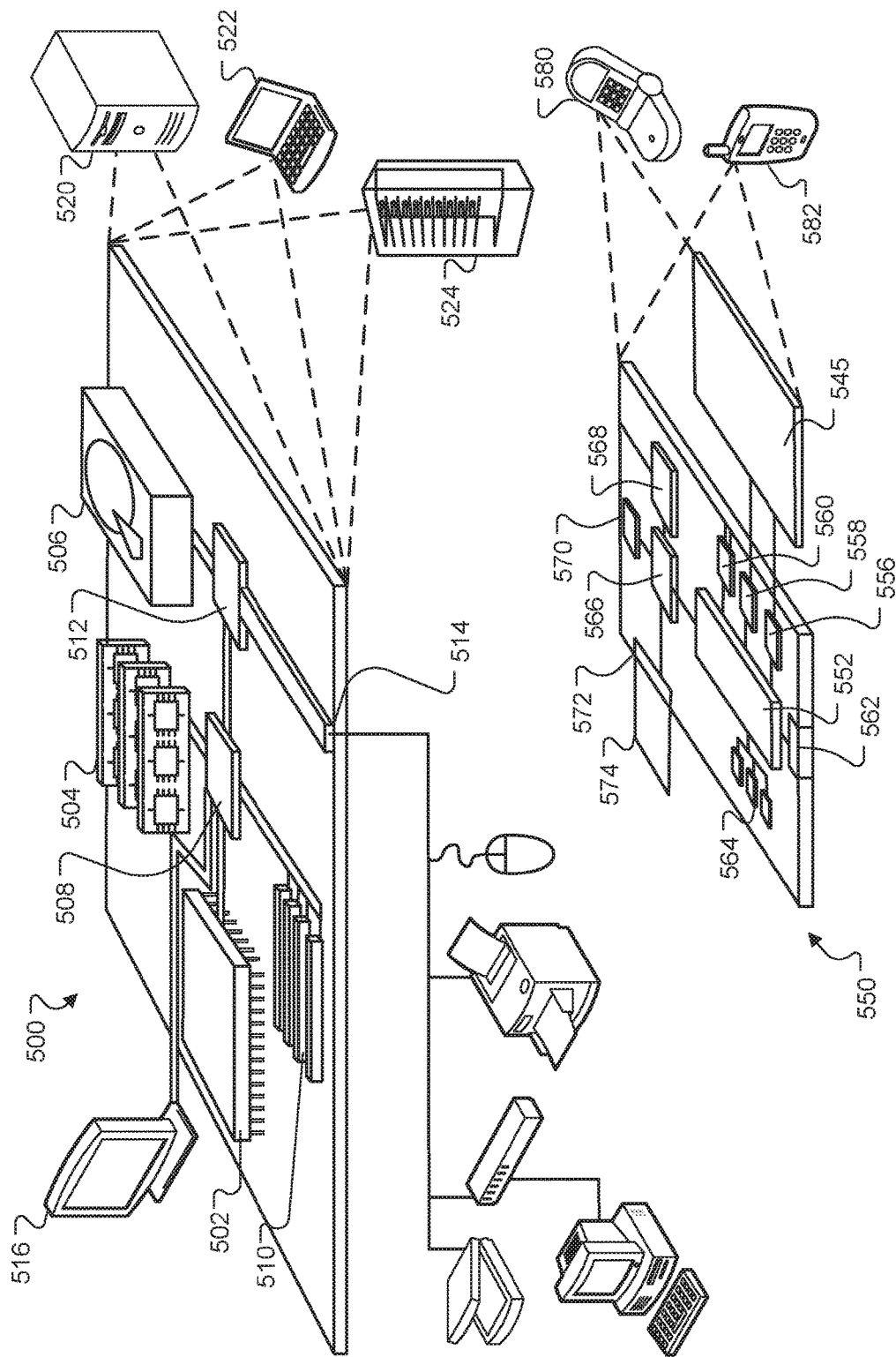
FIG. 5 shows a block diagram of a computing system that can be used in connection with computer-implemented methods described in this specification.

FIG. 5 is a block diagram of computing devices 500, 550 that may be used to implement the systems and methods described in this document, as either a client or as a server or plurality of servers. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method comprising:
   receiving, via a user interface of a client device, a user selection of a plurality of applications based on specific criteria, wherein the specific criteria is a predicted clinical benefit of an application for a patient;

for each application of the plurality of applications associated with the client device:

receiving, by one or more processors, data streams from the application of a client device, the data streams indicative of one or more of health characteristics of a patient and one or more locations visited by the patient, the patient associated with the client device;

determining, by the one or more processors, a utilization attribute of the application using a corresponding data stream;

generating, by the one or more processors, an output representing a predicted clinical benefit value of the application based on the utilization attribute for the application;

generating, by the one or more processors, (i) anonymized healthcare data by filtering personally identifiable information (PII) from the received data streams and (ii) an anonymized utilization attribute by filtering PII from the utilization attribute for the application;

detecting, by the one or more processors, recurrent patterns based on analysis of the anonymized utilization attribute for each application and the anonymized healthcare data for patients that use the plurality of applications, the anonymized utilization attribute for each application indicating a respective measure of effectiveness of the application with reference to how often a patient accesses the application and clinically benefits from the application;

generating, by the one or more processors and based on the detected recurrent patterns, a patient archetype that is descriptive of a health condition that affects each of a plurality of patients assigned to the patient archetype;

determining, by the one or more processors, the predicted clinical benefit value of each application of the plurality of applications based on at least a patient's prior use of each application over a predetermined time period, wherein the predicted clinical benefit value reflects an actual clinical benefit that improves the health condition associated with the patient archetype;

comparing, by the one or more processors, the predicted clinical benefit value of each application to a threshold value;

ranking, by the one or more processors, each application of the plurality of applications satisfying the threshold value according to their predicted clinical benefit value; and in response to the ranking, displaying, by the one or more processors, icons associated with each application of the plurality of applications on the user interface of the client device in a ranked vertical manner based on the predicted clinical benefit value of each application of the plurality of applications.

2. The method of claim 1, comprising:

receiving, by the one or more processors, data that indicates a medical characteristic of the patient; and determining, by the one or more processors, that the medical characteristic corresponds to a characteristic of a patient group included in the patient archetype.

3. The method of claim 2, wherein the medical characteristic is associated with a medical condition of the patient and the actual clinical benefit of each application of the plurality of applications is provided based on application content that is determined to be advantageous for improving the medical condition of the patient.

4. The method of claim 1, further comprising:

identifying, by the one or more processors, one or more characteristics included in the patient archetype; and determining, by the one or more processors, the output representing the predicted clinical benefit value of the application exceeds the threshold value with reference to the one or more characteristics in the patient archetype.

5. The method of claim 1, wherein the anonymized utilization attribute for each application is determined using application-specific data comprising:

i) application ratings about the application;

ii) content of the application that are indicated as being advantageous for improving medical conditions of patients; and iii) demographic data that indicates attributes of patients that use the application.

6. The method of claim 1, wherein generating the patient archetype comprises:

processing, by the one or more processors, the anonymized utilization attribute for each application and the anonymized healthcare data for patients derived from usage of the plurality of applications; and in response to processing, generating, by the one or more processors, the patient archetype, wherein the patient archetype is among a set of patient archetypes that are descriptive of one or more patient groups.

7. The method of claim 1, further comprising:

generating, by the one or more processors, predictive outputs that identify at least one health outcome that is associated with use of the application; and determining, by the one or more processors, that the application provides the actual clinical benefit based on the predictive outputs generated.

8. A computing system, comprising: a computing server; one or more processors; and one or more non-transitory machine-readable storage devices storing instructions that are executable by the one or more processors to cause performance of operations that comprise:

receiving, via a user interface of a client device, a user selection of a plurality of applications based on specific criteria, wherein the specific criteria is a predicted clinical benefit of an application for a patient;

for each application of the plurality of applications associated with the client device:

receiving, by one or more processors, data streams from the application of the client device, the data streams indicative of one or more of health characteristics of the patient and one or more locations visited by the patient, the patient associated with the client device;

determining, by the one or more processors, a utilization attribute of the application using a corresponding data stream; generating, by the one or more processors, an output representing a predicted clinical benefit value of the application based on the utilization attribute for the application;

generating, by the one or more processors, (i) anonymized healthcare data by filtering personally identifiable information (PII) from the received data streams and (ii) an anonymized utilization attribute by filtering PII from the utilization attribute for the application; detecting, by the one or more processors, recurrent patterns based on analysis of the anonymized utilization attribute for each application and the anonymized healthcare data for patients that use the plurality of applications, the anonymized utilization attribute for each application indicating a respective measure of effectiveness of the application with reference to how often a patient accesses the application and clinically benefits from the application;

generating, by the one or more processors and based on the detected recurrent patterns, a patient archetype that is descriptive of a health condition that affects each of a plurality of patients assigned to the patient archetype;

determining, by the one or more processors, the predicted clinical benefit value of each application of the plurality of applications based on at least a patient's prior use of each application over a predetermined time period, wherein the predicted clinical benefit value reflects an actual clinical benefit that improves the health condition associated with the patient archetype;

comparing, by the one or more processors, the predicted clinical benefit value of each application to a threshold value;

ranking, by the one or more processors, each application of the plurality of applications satisfying the threshold value according to their predicted clinical benefit value; and in response to the ranking, displaying, by the one or more processors, icons associated with each application of the plurality of applications on the user interface of the client device in a ranked vertical manner based on the predicted clinical benefit value of each application of the plurality of applications.

9. The computing system of claim 8, wherein the operations comprise:
receiving, by the one or more processors, data that indicates a medical characteristic of the patient; and
determining, by the one or more processors, that the medical characteristic corresponds to a characteristic of a patient group included in the patient archetype.

10. The computing system of claim 9, wherein the medical characteristic is associated with a medical condition of the patient and the actual clinical benefit of the application is provided based on application content that is determined to be advantageous for improving the medical condition of the patient.

11. The computing system of claim 8, further comprising:
identifying, by the one or more processors, one or more characteristics included in the patient archetype; and
determining, by the one or more processors, the output representing the predicted clinical benefit value of the application exceeds the threshold value with reference to the one or more characteristics in the patient archetype.

12. The computing system of claim 8, wherein the anonymized utilization attribute for each application is determined using application-specific data comprising:
i) application ratings about the application;
ii) technical attributes and functions of the application that are indicated as being advantageous for improving medical conditions of patients; and
iii) demographic data that indicates attributes of patients that use the application.

13. The computing system of claim 8, wherein generating the patient archetype comprises:
processing, by the one or more processors, the anonymized utilization attribute for each application and the anonymized healthcare data for patients derived from usage of the plurality of applications; and
in response to processing, generating, by the one or more processors, the patient archetype, wherein the patient archetype is among a set of patient archetypes that are descriptive of one or more patient groups.

14. The computing system of claim 8, further comprising:
generating, by the one or more processors, predictive outputs that identify at least one health outcome that is associated with use of the application; and
determining, by the one or more processors, that the application provides the predicted clinical benefit value based on the predictive outputs generated.

15. One or more non-transitory machine-readable storage devices storing instructions for implementing a method using a computing server, the instructions being executable by one or more processing devices to cause performance of operations comprising:
receiving, via a user interface of a client device, a user selection of a plurality of applications based on specific criteria, wherein the specific criteria is a predicted clinical benefit of an application for a patient;
for each application of the plurality of applications associated with the client device:
receiving, by one or more processors, data streams from the application of a client device, the data streams indicative of one or more of health characteristics of the patient and one or more locations visited by the patient, the patient associated with the client device;
determining, by the one or more processors, a utilization attribute of the application using a corresponding data stream;
generating, by the one or more processors, an output representing a predicted clinical benefit value of the application based on the utilization attribute for the application;
generating, by the one or more processors, (i) anonymized healthcare data by filtering personally identifiable information (PII) from the received data streams and (ii) an anonymized utilization attribute by filtering PII from the utilization attribute for the application;
detecting, by the one or more processors, recurrent patterns based on analysis of the anonymized utilization attribute for each application and the anonymized healthcare data for patients that use the plurality of applications, the anonymized utilization attribute for each application indicating a respective measure of effectiveness of the application with reference to how often a patient accesses the application and clinically benefits from the application;
generating, by the one or more processors and based on the detected recurrent patterns, a patient archetype that is descriptive of a health condition that affects each of a plurality of patients assigned to the patient archetype;
determining, by the one or more processors, the predicted clinical benefit value of each application of the plurality of applications based on at least a patient's prior use of each application over a predetermined time period, wherein the predicted clinical benefit value reflects an actual clinical benefit that improves the health condition associated with the patient archetype;
comparing, by the one or more processors, the predicted clinical benefit value of each application to a threshold value;
ranking, by the one or more processors, each application of the plurality of applications satisfying the threshold value according to their predicted clinical benefit value; and in response to the ranking, displaying, by the one or more processors, icons associated with each application of the plurality of applications on the user interface of the client device in a ranked vertical manner based on the predicted clinical benefit value of each application of the plurality of applications.

16. The one or more non-transitory machine-readable storage devices of claim 15, wherein the operations comprise:
receiving, by the one or more processors, data that indicates a medical characteristic of the patient; and
determining, by the one or more processors, that the medical characteristic corresponds to a characteristic of a patient group included in the patient archetype.

17. The method of claim 1, wherein the utilization attribute is determined based on at least one of (i) a number of downloads of each application of the plurality of applications, (ii) a retention rate of each application of the plurality of applications on the client device, and (iii) a result of parsing review comments written about health benefits of each application of the plurality of applications.

18. The method of claim 1, wherein the respective measure of effectiveness of the application with reference to how often a patient accesses the application and clinically benefits from the application comprises at least one of (i) an ability of the application to provide a clinical benefit to the patient, (ii) aid in a medical treatment of the patient, and (iii) aid in making economic decisions related to medical progress of the patient.

19. The method of claim 1, further comprises determining that the predicted clinical benefit value exceeds the threshold value.

20. The method of claim 1, wherein detecting the recurrent patterns based on the analysis of the anonymized utilization attribute for each application and the anonymized healthcare data for the patients that use the plurality of applications further comprises:
detecting, by the one or more processors, at least one of a daily step count, a daily heart rate, and an exercise frequency of the patient;
determining, by the one or more processors, geo-location information of each patient; and
determining, by the one or more processors, whether the patient visits locations associated with healthy or unhealthy practices based on the determined geo-location information.

21. The computer-implemented method of claim 1, wherein the data streams indicative of one or more of the health characteristics of the patient and one or more locations visited by the patient comprise a frequency at which the patient exercises and a frequency at which the patient visits locations that are associated with healthy or unhealthy practices.

22. The computer-implemented method of claim 1, further comprising:
generating, by the one or more processors and for display at the user interface, an output recommendation indicating an application by a patient assigned to the patient archetype that is predicted to improve the health condition that affects the patient;
in response to generating the output recommendation indicating usage of the application by the patient assigned to the patient archetype, providing, by the one or more processors, data indicating the output recommendation indicating the application to the client device of the patient;
in response, receiving, by the one or more processors, a second data stream from the application from the output recommendation of the client device of the patient;
determining, by the one or more processors, a second utilization attribute of the application using the second data stream;
generating, by the one or more processors, a second output representing a second predicted clinical benefit value of the application based on the second utilization attribute for the application;
generating, by the one or more processors, (i) second anonymized healthcare data by filtering second PII from the received second data streams and (ii) a second anonymized utilization attribute by filtering the second PII from the utilization attribute for the application;
comparing, by the one or more processors, the second anonymized healthcare data to the anonymized healthcare data;
in response to comparing the second anonymized healthcare data to the anonymized healthcare data, determining, by the one or more processors, a change in a health status of the patient; and
generating, by the one or more processors, a second patient archetype that is descriptive of a second health condition that affects the patient using the second anonymized healthcare data, the second patient archetype different from the patient archetype.

23. The computer-implemented method of claim 22, comprising:
in response to generating the second patient archetype, determining, by the one or more processors, a second application to provide as a recommendation to the patient, the second application providing a clinical benefit that improves the health condition associated with the second patient archetype; and
providing, by the one or more processors, a second output recommendation to instruct the patient to use the second application.

24. The computer-implemented method of claim 1, comprising:
comparing, by the one or more processors, the received data streams to data indicative of a geographic location;
in response to comparing, determining, by the one or more processors, whether one or more of the locations visited by the patient in the received data streams match to the geographic location;
in response to determining that one or more of locations visited by the patient in the received data streams match to the geographic location, analyzing, by the one or more processors, the received data streams related to the one or more locations visited by the patient to determine whether the patient visited at least one of an unhealthy food location, a healthy food location, and a vitamin shop; and
in response to determining that the patient visited at least one of the unhealthy food location, the healthy food location, and the vitamin shop, determining, by the one or more processors, the health characteristics of the patient using the received data streams based on the one or more determined locations of the patient.

* * * * *